United States Patent [19]

Oppong et al.

[11] Patent Number: 5,374,631

[45] Date of Patent: Dec. 20, 1994

[54] SYNERGISTIC COMBINATIONS OF IODOPROPARGYL COMPOUNDS WITH HEXAHYDRO-1,3,5-TRIS(2-HYDROXYETHYL)-S-TRIAZINE IN CONTROLLING FUNGAL AND BACTERIAL GROWTH IN AQUEOUS FLUIDS

[75] Inventors: David Oppong, Memphis; S. Rao Rayudu, Germantown, both of Tenn.

[73] Assignee: Buckman Laboratories International, Inc., Tenn.

[21] Appl. No.: 13,552

[22] Filed: Jan. 27, 1993

Related U.S. Application Data

[63] Continuation of Ser. No. 606,819, Oct. 31, 1990, abandoned.

[51] Int. Cl.$^5$ .................... A01N 43/66; A01N 47/10
[52] U.S. Cl. .................................. 514/241; 514/479
[58] Field of Search ........................... 514/241, 479

[56] References Cited

U.S. PATENT DOCUMENTS

| | | | |
|---|---|---|---|
| 3,879,445 | 4/1975 | Gray et al. | 260/469 |
| 3,923,870 | 12/1975 | Singer | 106/15 |
| 3,970,755 | 7/1976 | Gazzard et al. | 424/263 |
| 4,158,655 | 6/1979 | Brady | 260/45.75 |
| 4,259,350 | 3/1981 | Morisawa et al. | 549/71 |
| 4,616,004 | 10/1986 | Edwards | 514/384 |
| 4,719,227 | 1/1988 | Schade et al. | 514/452 |
| 4,830,657 | 5/1989 | Jakubowski et al. | 514/327 |
| 4,844,891 | 7/1989 | Rosen et al. | 424/76.4 |
| 4,945,109 | 7/1990 | Rayudu | 514/478 |
| 4,952,773 | 6/1986 | Tanaka et al. | 71/88 |

FOREIGN PATENT DOCUMENTS

| | | |
|---|---|---|
| 60-71009 | 4/1985 | Japan . |
| 1476862 | 6/1977 | United Kingdom ......... 514/241 |

OTHER PUBLICATIONS

Bennett, E. O., "The Deterioration of Metalworking Fluids", Prog. Industrial Microbiology, 13:121 (1974).

*Primary Examiner*—Allen J. Robinson
*Assistant Examiner*—Brian Bembenick
*Attorney, Agent, or Firm*—Finnegan, Henderson, Farabow, Garrett & Dunner

[57] ABSTRACT

Synergistic combinations of iodopropargyl compounds and hexahydro-1,3,5-tris(2-hydroxyethyl)-s-triazine for use in controlling the growth of microorganisms, such as fungi and bacteria in aqueous fluids, such as metalworking fluids.

2 Claims, No Drawings 5,374,631

SYNERGISTIC COMBINATIONS OF IODOPROPARGYL COMPOUNDS WITH HEXAHYDRO-1,3,5-TRIS(2-HYDROXYETHYL)-S-TRIAZINE IN CONTROLLING FUNGAL AND BACTERIAL GROWTH IN AQUEOUS FLUIDS

This application is a continuation of application Ser. No. 07/060,819, filed Oct. 31, 1990, now abandoned.

The invention is directed to synergistic antimicrobial combinations of an iodopropargyl compound with hexahydro-1,3,5-tris(2-hydroxyethyl)-s-triazine and use of such combinations in controlling fungal and/or bacterial growth in aqueous systems, particularly in metalworking fluids, such as soluble oil, semi-synthetic and synthetic metalworking fluids.

BACKGROUND OF THE INVENTION

Iodopropargyl compounds, i.e. compounds containing a propargyl group and an iodine on the acetylenic carbon, are known to be useful in controlling bacteria and fungi in various aqueous systems. U.S. Pat. Nos. 4,259,350; 4,719,227; 4,616,004; 3,923,870; 4,592,773 give various examples of iodopropargyl compounds with microbicidal properties. The disclosure of each of these patents identified in this paragraph is incorporated specifically herein by reference.

One such iodopropargyl compound is iodopropargyl carbamate manufactured by Buckman Laboratories, Inc. as BL-1120 product. The preparation and use of iodopropargyl carbamate as a microbicide and a preservative is described in U.S. Pat. No. 4,945,109, the disclosure of which is incorporated herein by reference.

Another such iodopropargyl compound is 3-iodopropargyl-N-butylcarbamate (IPBC). This compound is manufactured and sold by Troy Chemical Company under various names such as Polyphase product, Polyphase AF-1 product, Polyphase NP-1 product, etc. IPBC is used in the metalworking fluid industry for controlling bacteria and fungi.

Although good microbicides, iodopropargyl compounds are expensive. Systems requiring high concentrations of iodopropargyl compounds are generally uneconomical.

Hexahydro-1,3,5-tris(2-hydroxyethyl)-s-triazine has been used in the metalworking fluid industry for a long time. This compound is sold as Grotan product, Busan 1060 product, etc. This compound is known in the art as "triazine".

As can be seen in Table 1 (see Samples 14–17), high concentrations of hexahydro-1,3,5-tris(2-hydroxyethyl)-s-triazine are required to control both bacteria and fungal growth in metalworking fluids.

One of the by-products of hexahydro-1,3,5-tris(2-hydroxyethyl)-s-triazine when used as a microbicide is formaldehyde. Because of the carcinogenic properties of formaldehyde, it is desirable to use compounds that produce formaldehyde in the smallest quantities possible. Unfortunately, when used in reasonable concentrations, i.e., concentrations which produce only small amounts of formaldehyde, triazines are ineffective against fungi.

Both of these types of products are used alone to control microorganisms in industrial fluids. Many industries, such as the machining industry, experience problems caused by microorganisms. Aqueous metalworking fluids or cutting fluids used in the machining industry are particularly susceptible to fouling caused by microorganisms. In machining operations, metalworking fluids are used primarily to reduce friction and heat, thereby reducing wear and prolonging the life of equipment.

Unfortunately, metalworking fluids have properties which are ideal for the growth of bacteria and fungi. Although bacteria are important in the biodeterioration of metalworking fluids, fungi and yeast play an important role as well. (Bennett, E. O., "The Deterioration of Metalworking Fluids", Prog. Industrial Microbiology, 13:121 (1974)).

Disadvantageously, these microorganisms can cause the buildup of slime/microbial deposits on machine surfaces, the clogging of jets and lines, the deterioration of the properties of the metalworking fluid itself, enhanced corrosion, and health and odor problems. When deteriorated by the growth of microorganisms, the metalworking fluid begins to deteriorate and lose many of its essential properties. The pH of the fluid may drop and other chemical changes may occur until the fluid can no longer provide adequate lubrication. At this point, the fluid must be replaced with fresh fluid, which is costly and results in loss of production time.

The previously-mentioned problems have resulted in the extensive use of biocides in metalworking fluid systems. Biocides may be incorporated in fluid concentrate or added to diluted fluids once they are in the holding tanks of the machine works.

There are many commercially available biocides, at least many of which disadvantageously have odor problems, or create hazards with respect to storage, use or handling, which limit the utility thereof. Consequently, workers in the art have continued to seek improved biocides.

Economic factors, particularly the cost of the biocide and the expense of its application, can also be important when choosing a particular biocide for use in metalworking fluid systems. The cost performance index of any biocide is derived from the basic cost of the material, its effectiveness per unit weight, the duration of its biocidal or biostatic effect in the system treated, and the ease and frequency of its addition to the system treated.

Workers in the art have sought a commercially available biocide capable of exhibiting a prolonged biocidal effect at normal use levels. Physical conditions, such as temperature and chemical reactivity with ingredients present in the system, often diminish or eliminate the effectiveness of prior art biocides known to the inventors. For example, many systems contain organic material which may react with a specific biocide or render it ineffective.

Metalworking fluid systems in which heavy microbial growth occurs can benefit from the practice of the present invention, which is described below. The practice of the present invention can also benefit many other aqueous systems, whether or not heavy microbial growth occurs, because it provides a more limited use of hexahydro-1,3,5-tris(2-hydroxyethyl)-s-triazine, a formaldehyde-producing biocide.

SUMMARY OF THE INVENTION

Synergistic combinations of an iodopropargyl compound and triazine do not appear to be known in the literature. An object of the present invention is to control fungal or bacterial growth in an aqueous system, such as a metalworking or cutting fluid, through the use of a synergistic combination of an iodopropargyl compound and a triazine.

A first embodiment of the present invention is a composition comprising (a) hexahydro-1,3,5-tris(2-hydroxyethyl)-s-triazine and (b) an iodopropargyl compound, the composition containing an amount of (a) and (b) synergistically effective to reduce the growth of microorganisms.

A second embodiment is metalworking fluid comprising (a) hexahydro-1,3,5-tris(2-hydroxyethyl)-s-triazine and (b) an iodopropargyl compound, the fluid containing an amount of (a) and (b) synergistically effective to reduce the growth of microorganisms in said fluid.

A third embodiment is a concentrated metalworking fluid comprising (a) hexahydro-1,3,5-tris(2-hydroxyethyl)-s-triazine and (b) an iodopropargyl compound, the concentrated fluid containing an amount of (a) and (b) synergistically effective to reduce the growth of microorganisms in the fluid when diluted and used at a metalworking site.

A fourth embodiment according to the invention is a method of controlling the growth of microorganisms in an aqueous fluid comprising the step of adding to the fluid a composition comprising (a) hexahydro-1,3,5-tris(2-hydroxyethyl)-s-triazine and (b) an iodopropargyl compound in a synergistically effective amount to control said growth.

A fifth embodiment is a method of controlling the growth of microorganisms in a diluted metalworking fluid comprising the step of separately adding to said diluted metalworking fluid: (a) a hexahydro-1,3,5-tris(2-hydroxyethyl)-s-triazine and (b) an iodopropargyl compound where the ratio of (a) to (b) after addition of both components is from about 1:99 to 99:1. The combined amount of separately added (a) and (b) is synergistically effective to control the growth of microorganisms in the fluid.

A sixth embodiment is a method of controlling the growth of microorganisms in a diluted metalworking fluid comprising the step of adding to a diluted metalworking fluid: (a) a hexahydro-1,3,5-tris(2-hydroxyethyl)-s-triazine and (b) an iodopropargyl compound wherein the ratio of (a) to (b) after addition of both components is from about 1:99 to 99:1. The combined amount of added (a) and (b) is synergistically effective to control the growth of micro-organisms in said fluid.

DETAILED DESCRIPTION OF THE INVENTION

Hexahydro-1,3,5-tris(2-hydroxyethyl)-s-triazine can be easily prepared starting from formaldehyde and 2-hydroxyethanolamine. This compound is presently sold as a solid or in varying concentrations in water under such commercial names as Grotan product, Busan 1060 product, etc.

An iodopropargyl compound for use in the present invention can be identified by the structure shown below:

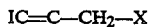

wherein X can be (1) oxygen which is part of an organic functional group; (2) nitrogen which is part of an organic functional group; (3) sulfur which is part of an organic functional group; or (4) carbon which is part of an organic functional group.

The functional group of which oxygen is a part is preferably an ether, ester or carbamate group. The functional group of which nitrogen is a part is preferably an amine, amide or carbamate group. The functional group of which sulfur is a part is preferably a thiol, thiane, sulfone or sulfoxide group. The organic functional group of which carbon is a part is preferably an ester, carbamate or alkyl group.

The iodopropargyl compound may be chosen from a wide variety of known chemicals based on the compatibility of these compounds with metalworking fluids or other aqueous systems in use. Compatibility is determined by criteria such as solubility in the fluid system and lack of reactivity with the fluid or other components in the fluid, i.e. formation of precipitates of the iodopropargyl compounds reduces the effectiveness of the microbicide. The compatability is readily determined by one of ordinary skill by adding the iodopropargyl compound to the fluid to be used. It is preferred that the iodopropargyl compound be freely soluble in the particular fluid resulting in a uniform solution.

Iodopropargyl carbamate is known to be compatible with soluble oil, semi-synthetic and synthetic metalworking fluids. One of the formulations of this compound, BL-1120 product manufactured by Buckman Laboratories, is a 20% emulsifiable concentrate.

Another such iodopropargyl compound is 3-iodopropargyl-N-butylcarbamate. One of the formulations of this compound is Polyphase AF-1 product which is a 40% emulsifiable concentrate.

In the following discussion of preferred embodiments, component (a) is a hexahydro-1,3,5-tris(2-hydroxyethyl)-s-triazine supplied as Busan 1060 product, a 78.5% solution in water. Component (b) is BL-1120 product which contains 20% of the active ingredient iodopropargyl carbamate or Polyphase AF-1 product which contains 40% of the active ingredient 3-iodopropargyl-N-butylcarbamate.

The ratio of component (a) to component (b) preferably ranges from 1:99 to 99:1, more preferably 20:80 to 80:20, most preferably 40:60 to 60:40. An 80:20 ratio is particularly preferred.

When two chemical microbiocides are combined into one product or added separately three results are possible:

(1) The resulting product would produce an additive (neutral) effect.
(2) The chemicals in the product would produce an antagonistic effect, or
(3) The chemicals in the product would produce a synergistic effect.

An additive effect has no economic advantage over the individual components. The antagonistic effect would produce a negative impact. Only synergism, which is much less likely than either an additive or antagonistic effect, would produce a positive effect and therefore would be of economic advantage.

It is well-known ill the microbicidal literature that there is no theoretical method to provide a reasonable likelihood of knowing, before actually testing, whether additive, antagonistic or synergistic effects will be obtained when two biocides are mixed to yield a new formulation.

The benefits of the invention are most evident in systems that are highly contaminated with microorganisms. These are systems with bacterial and fungal counts greater than $1.0 \times 10^6$/mL which are incapable of experiencing substantial count reduction when treated separately with low dosages of either an iodopropargyl compound or hexahydro-1,3,5-tris(2-hydroxyethyl)-s-triazine.

In these systems, a low concentration of hexahydro-1,3,5-tris(2-hydroxyethyl)-s-triazine biocide or an iodopropargyl compound fails to provide adequate preservation. Evidence of adequate preservation or control is reduction to and maintanance of a bacterial count of less than $1 \times 10^5$ per mL and fungal count of less than $1 \times 10^3$ per mL for a period of not less than about six weeks.

One of the unique features of this invention is that when hexahydro-1,3,5-tris(2-hydroxyethyl)-s-triazine is used in conjunction with an iodopropargyl compound, it is possible in many instances, at certain concentrations and ratios of components, to achieve excellent fluid preservation, i.e. reducing the total fungal or bacterial count to undetectable limits and maintaining it at that level. When either of the biocides is used alone, each fails to achieve and maintain such a low level of microbial growth.

The synergistic activity of the combinations described above has been confirmed using standard laboratory techniques as illustrated below. The following examples are intended to illustrate, not limit, the present invention.

The test method employed was the Standard Method for the Evaluation of Antimicrobial Agents in Aqueous Metalworking Fluids (ASTM Designation: E686-80).

The ASTM test is a multiple challenge test designed to simulate industrial conditions. A formulation containing both biocides is added to 600 mL aliquots of a metalworking fluid dilution. Controls contained only one of the biocides or no biocide.

The metalworking fluid samples are then inoculated with 1 mL of a mixed, partially defined microbial culture to give an initial bacterial count of approximately $1 \times 10^6$ and fungal count of not less than $1 \times 10^3$ and aerated continuously. The system is aerated to provide oxygen for the growth of the microorganisms and also to simulate the industrial rolling of the coolant.

Every week, for a minimum of 6 weeks or until the test fails, the metalworking fluid samples are measured for microbial growth. This is done by enumerating the bacteria and fungi using standard plate-counting techniques.

The microorganisms used in the metalworking fluid innoculum included:
1) "Wild" fungi and bacteria obtained from a spoiled industrial fluid.
2) *Staphylococcus aureus*
3) *Pseudomonas aeruginosa*
4) *Klebsiella pneumoniae*
5) *Escherichia coli*

After six weeks a bacterial count of less than $1 \times 10^5$ per mL and fungal count of less than $1 \times 10^3$ per mL was indicative of excellent preservation. This was also used in the Examples as an endpoint.

In general, however, an effective fungicidal and bactericidal response can be obtained when the synergistic combination is employed in concentrations ranging from about 0.1 to about 5000 ppm of hexahydro-1,3,5-tris(2-hydroxyethyl)-s-triazine, preferably 0.1 to 1000 ppm, and from about 0.1 to about 5000 ppm of an iodopropargyl compound, preferably 0.1 to 500 ppm.

EXAMPLE 1

Synergistic combinations of hexahydro-1,3,5-tris(2-hydroxyethyl)-s-triazine and iodopropargyl carbamate for use in soluble oil metalworking fluids.

Component (a) is a 78.5% solution of hexahydro-1,3,5-tris(2-hydroxyethyl)-s-triazine, Busan 1060 product and component (b) is a 20% solution of iodopropargyl carbamate, BL-1120 product. Components (a) and (b) are added in different weight ratios and amounts to the diluted metalworking fluids and tested according to the test methods described previously.

The results are given in Table 1. As can be seen in Table 1, Samples 2 through 13 all are synergistically effective in the control of bacteria and fungal growth. Sample 5 particularly shows the effectiveness of the combination of components (a) and (b) at low concentrations where a combination of 250 ppm of component (a) and 25 ppm of component (b) produces synergistic effects. In contrast, when used separately, 2000 ppm of component (a) or 500 ppm of component (b) are required to preserve the soluble oil metalworking fluid for six weeks.

TABLE 1

Preservation properties of combinations of (a) hexahydro-1,3,5-tris(2-hydroxyethyl)-s-triazine and (b) iodopropargyl carbamate in a soluble metalworking fluid.

| Sample | Ratio of (a) to (b) | Component (a) ppm | Component (b) ppm | Bacterial Count cfu/mL | Fungal Count cfu/mL |
|---|---|---|---|---|---|
| 1 | — | 0 | 0 | $2.3 \times 10^7$ | $10^3$ |
| 2 | 1:1 | 250 | 250 | 30 | <10 |
| 3 | 5:2 | 250 | 100 | $1.4 \times 10^2$ | <10 |
| 4 | 5:1 | 250 | 50 | $2.3 \times 10^2$ | 30 |
| 5 | 10:1 | 250 | 25 | $3.6 \times 10^2$ | <10 |
| 6 | 2:1 | 500 | 250 | <10 | <10 |
| 7 | 5:1 | 500 | 100 | <10 | <10 |
| 8 | 10:1 | 500 | 50 | <10 | <10 |
| 9 | 20:1 | 500 | 25 | <10 | <10 |
| 10 | 4:1 | 1000 | 250 | <10 | <10 |
| 11 | 10:1 | 1000 | 100 | <10 | <10 |
| 12 | 20:1 | 1000 | 50 | <10 | <10 |
| 13 | 40:1 | 1000 | 25 | <10 | <10 |
| 14 | | 250 | — | $2.6 \times 10^7$ | $2.5 \times 10^5$ |
| 15 | | 500 | — | $3.0 \times 10^7$ | $1.3 \times 10^6$ |
| 16 | | 1000 | — | $7.1 \times 10^7$ | $5.0 \times 10^6$ |
| 17 | | 2000 | — | <10 | <10 |
| 18 | | — | 100 | $5.1 \times 10^6$ | <10 |
| 19 | | — | 250 | $6.5 \times 10^6$ | <10 |
| 20 | | — | 500 | $2.9 \times 10^3$ | <10 |

EXAMPLE 2

Synergistic combinations for hexahydro-1,3,5-tris(2-hydroxyethyl)-s-triazine and iodopropargyl carbamate for use in synthetic metalworking fluids.

Component (a) is a 78.5% solution of hexahydro-1,3,5-tris(2-hydroxyethyl)-s-triazine, Busan 1060 product, and component (b) is a 20% solution of iodopropargyl carbamate, BL-1120 product. Components (a) and (b) are added in different weight ratios and amounts to the diluted metalworking fluids and tested according to the test methods described previously.

The results are given in Table 2. As can be seen in Table 2, samples 2 through 13 show a synergistic result in the effective control of bacterial and fungal growth in the metalworking fluid.

When used alone, either 2000 ppm of component (a) (Sample 17) or 250 ppm of component (b) (Sample 22) are required to preserve the synthetic metalworking fluid for six weeks. In contrast, when used in combination, only 250 ppm of component (a) and only 10 ppm of component (b) are needed to produce the same effect.

TABLE 2

Preservation properties of combinations of
(a) hexahydro-1,3,5-tris(2-hydroxyethyl)-s-triazine and
(b) iodopropargyl carbamate in a synthetic metalworking fluid.

| Sample | Ratio of (a) to (b) | Component (a) ppm | Component (b) ppm | Bacterial Count cfu/mL | Fungal Count cfu/mL |
|---|---|---|---|---|---|
| 1 | — | 0 | 0 | $5.6 \times 10^8$ | $1.9 \times 10^6$ |
| 2 | 25:1 | 250 | 10 | 20 | <10 |
| 3 | 10:1 | 250 | 25 | <10 | <10 |
| 4 | 5:1 | 250 | 50 | <10 | <10 |
| 5 | 5:2 | 250 | 100 | <10 | <10 |
| 6 | 50:1 | 500 | 10 | <10 | <10 |
| 7 | 20:1 | 500 | 25 | <10 | <10 |
| 8 | 10:1 | 500 | 50 | <10 | <10 |
| 9 | 5:1 | 500 | 100 | <10 | <10 |
| 10 | 100:1 | 1000 | 10 | <10 | <10 |
| 11 | 40:1 | 1000 | 25 | <10 | <10 |
| 12 | 20:1 | 1000 | 50 | <10 | <10 |
| 13 | 10:1 | 1000 | 100 | <10 | <10 |
| 14 | | 250 | — | $2.4 \times 10^8$ | $4.3 \times 10^6$ |
| 15 | | 500 | — | $1.4 \times 10^8$ | $2.6 \times 10^6$ |
| 16 | | 1000 | — | $9.0 \times 10^7$ | $2.8 \times 10^5$ |
| 17 | | 2000 | — | <10 | 40 |
| 18 | | — | 10 | $7.9 \times 10^7$ | $1.1 \times 10^5$ |
| 19 | | — | 25 | $2.3 \times 10^7$ | $2.5 \times 10^2$ |
| 20 | | — | 50 | $3.4 \times 10^6$ | <10 |
| 21 | | — | 100 | $1.7 \times 10^6$ | <10 |
| 22 | | — | 250 | <10 | <10 |

EXAMPLE 3

Synergistic combinations of hexahydro-1,3,5-tris(2-hydroxyethyl)-s-triazine and iodopropargyl carbamate for use in semi-synthetic metalworking fluids.

Component (a) is a 78.5% solution of hexahydro-1,3,5-tris(2-hydroxyethyl)-s-triazine, Busan 1060 product, and component (b) is a 20% solution of iodopropargyl carbamate, BL-1120 product. Components (a) and (b) are added in different weight ratios and amounts to the diluted metalworking fluids and tested according to the test methods described previously.

The results are given in Table 3. As can be seen in Table 3, samples 3 through 13 show a synergistic result in the effective control of bacterial and fungal growth in the metalworking fluid. When used by themselves either 2000 ppm of component (a) (Sample 17) or 100 ppm of component (b) (Sample 21) are required to produce the preservative effect. But a combination of 250 ppm of component (a) and 25 ppm of component (b) (Sample 3) can produce the same preservative effect.

TABLE 3

Preservation properties of combinations of
(a) hexahydro-1,3,5-tris(2-hydroxyethyl)-s-triazine and (b)
iodopropargyl carbamate in a semi-synthetic metalworking fluid.

| Sample | Ratio of (a) to (b) | Component (a) ppm | Component (b) ppm | Bacterial Count cfu/mL | Fungal Count cfu/mL |
|---|---|---|---|---|---|
| 1 | — | 0 | 0 | $1.1 \times 10^8$ | $9 \times 10^5$ |
| 2 | 25:1 | 250 | 10 | <10 | $1.0 \times 10^6$ |
| 3 | 10:1 | 250 | 25 | <10 | <10 |
| 4 | 5:1 | 250 | 50 | <10 | <10 |
| 5 | 5:2 | 250 | 100 | <10 | <10 |
| 6 | 50:1 | 500 | 10 | <10 | $1.7 \times 10^2$ |
| 7 | 20:1 | 500 | 25 | <10 | <10 |
| 8 | 10:1 | 500 | 50 | <10 | <10 |
| 9 | 5:1 | 500 | 100 | <10 | <10 |
| 10 | 100:1 | 1000 | 10 | <10 | <10 |
| 11 | 40:1 | 1000 | 25 | <10 | <10 |
| 12 | 20:1 | 1000 | 50 | <10 | <10 |
| 13 | 10:1 | 1000 | 100 | <10 | <10 |
| 14 | | 250 | — | $1.0 \times 10^8$ | $2.0 \times 10^6$ |
| 15 | | 500 | — | $6.6 \times 10^9$ | $1.0 \times 10^6$ |
| 16 | | 1000 | — | $4.0 \times 10^7$ | $2.0 \times 10^6$ |
| 17 | | 2000 | — | <10 | <10 |
| 18 | | — | 10 | $1.6 \times 10^9$ | $8 \times 10^5$ |
| 19 | | — | 25 | $2 \times 10^9$ | $4 \times 10^4$ |
| 20 | | — | 50 | $4.5 \times 10^6$ | <10 |
| 21 | | — | 100 | $2.7 \times 10^2$ | <10 |
| 22 | | — | 250 | <10 | <10 |

EXAMPLE 4

Synergistic combinations of hexahydro-1,3,5-tris(2-hydroxyethyl)-s-triazine and 3-iodopropargyl-N-butyl carbamate to preserve a soluble oil metalworking fluid.

Component (a) is a 78.5% solution of hexahydro-1,3,5-tris(2-hydroxyethyl)-s-triazine, Busan 1060 product, and component (b) is 40% solution of 3-iodopropargyl-N-butyl carbamate, Polyphase AF-1 product. Component (a) and component (b) are added in different weight ratios and amounts to the dilute metalworking fluid and tested according to the test method described previously. The results are given in Table 4.

As can be seen in Table 4, samples 3 through 10 show a synergistic result in the effective control of bacterial and fungal growth in the metalworking fluid. A low-concentration combination of 250 ppm of component (a) and 50 ppm of component (b) (Sample 3) produces the synergistic preservation effect whereas when used alone either 2000 ppm of component (a) (Sample 14) or more than 100 ppm of component (b) (Sample 18) are required to produce a similar preservative effect.

TABLE 4

Preservation properties of combinations of (a) hexahydro-1,3,5- tris(2-hydroxyethyl)-s-triazine and (b) 3-iodopropargyl-N-butyl carbamate in a soluble oil metalworking fluid.

| Sample | Ratio of (a) to (b) | Component (a) ppm | Component (b) ppm | Bacterial Count cfu/mL | Fungal Count cfu/mL |
|---|---|---|---|---|---|
| 1 | — | 0 | 0 | $4.7 \times 10^7$ | $10^3$ |
| 2 | 10:1 | 250 | 25 | $10^6$ | $3.0 \times 10^5$ |
| 3 | 5:1 | 250 | 50 | $2.6 \times 10^2$ | <10 |
| 4 | 2.5:1 | 250 | 100 | $1.2 \times 10^2$ | <10 |
| 5 | 20:1 | 500 | 25 | 70 | <10 |
| 6 | 10:1 | 500 | 50 | 50 | <10 |
| 7 | 5:1 | 500 | 100 | $2.8 \times 10^2$ | <10 |
| 8 | 40:1 | 1000 | 25 | <10 | <10 |
| 9 | 20:1 | 1000 | 50 | 30 | <10 |
| 10 | 10:1 | 1000 | 100 | 80 | <10 |
| 11 | | 250 | — | $2.6 \times 10^7$ | $2.5 \times 10^5$ |
| 12 | | 500 | — | $3.0 \times 10^7$ | $1.3 \times 10^6$ |
| 13 | | 1000 | — | $7.1 \times 10^7$ | $5.0 \times 10^6$ |
| 14 | | 2000 | — | <10 | <10 |
| 15 | | — | 10 | $7.5 \times 10^7$ | $1.2 \times 10^3$ |
| 16 | | — | 25 | $5.3 \times 10^7$ | $10^3$ |
| 17 | | — | 50 | $4.4 \times 10^7$ | $10^2$ |
| 18 | | — | 100 | $3.6 \times 10^7$ | $10^2$ |

EXAMPLE 5

Synergistic combinations of hexahydro-1,3,5-tris(2-hydroxyethyl)-s-triazine and 3-iodopropargyl-N-butyl carbamate to preserve a semi-synthetic metalworking fluid.

Component (a) is a 78.5% solution of hexahydro-1,3,5-tris(2-hydroxyethyl)-s-triazine, Busan 1060 product, and component (b) is 40% solution of 3-iodopropargyl-N-butyl carbamate, Polyphase AF-1 product. Component (a) and component (b) are added in different weight ratios and amounts to the dilute metalworking fluid and tested according to the test method described previously. The results are given in Table 5.

As can be seen in Table 5, samples 2, 3 and 4 show a synergistic result in the effective control of bacterial and fungal growth in the metalworking fluid. When used alone, 2000 ppm of component (a) (Sample 8) and more than 50 ppm of component (b) (Sample 11) are required to preserve the metalworking fluid.

TABLE 5

Preservation properties of combinations of (a) hexahydro-1,3,5-tris(2-hydroxyethyl)-s-triazine and (b) 3-iodopropargyl-N-butyl carbamate in a semi-synthetic metalworking fluid.

| Sample | Ratio of (a) to (b) | Component (a) ppm | Component (b) ppm | Bacterial Count cfu/mL | Fungal Count cfu/mL |
|---|---|---|---|---|---|
| 1 | — | 0 | 0 | $1.6 \times 10^8$ | $8.0 \times 10^5$ |
| 2 | 10:1 | 250 | 25 | 60 | <10 |
| 3 | 50:1 | 500 | 10 | <10 | <10 |
| 4 | 100:1 | 1000 | 10 | <10 | <10 |
| 5 | — | 250 | — | $1.0 \times 10^8$ | $2.0 \times 10^6$ |
| 6 | — | 500 | — | $6.6 \times 10^9$ | $1.0 \times 10^6$ |
| 7 | — | 1000 | — | $4.0 \times 10^7$ | $2.0 \times 10^6$ |
| 8 | — | 2000 | — | <10 | <10 |
| 9 | — | — | 10 | $5.2 \times 10^7$ | $10^5$ |
| 10 | — | — | 25 | $6.3 \times 10^7$ | $10^4$ |
| 11 | — | — | 50 | $5.0 \times 10^7$ | <10 |

EXAMPLE 6

Synergistic combinations of hexahydro-1,3,5-tris(2-hydroxyethyl)-s-triazine and 3-iodopropargyl-N-butyl carbamate to preserve synthetic metalworking fluid.

Component (a) is a 78.5% solution of hexahydro-1,3,5-tris(2-hydroxyethyl)-s-triazine, Busan 1060 product and component (b) is 40% solution of 3-iodopropargyl-N-butyl carbamate, Polyphase AF-1 product. Component (a) and component (b) are added in different weight ratios and amounts to the dilute metalworking fluid and tested according to the test method described previously. The results are given in Table 6.

As can be seen in Table 6, samples 2, 3 and 4 show a synergistic result in the effective control of bacterial and fungal growth in the metalworking fluid. When used alone either 2000 ppm of component (a) (Sample 8) or more than 50 ppm of component (b) (Sample 11) are required to produce the same effect.

TABLE 6

Preservation properties of combinations of (a) hexahydro-1,3,5-tris(2-hydroxyethyl)-s-triazine and (b) 3-iodopropargyl-N-butyl carbamate in a synthetic metalworking fluid.

| Sample | Ratio of (a) to (b) | Component (a) ppm | Component (b) ppm | Bacterial Count cfu/mL | Fungal Count cfu/mL |
|---|---|---|---|---|---|
| 1 | — | 0 | 0 | $5.0 \times 10^7$ | $5.5 \times 10^5$ |
| 2 | 10:1 | 250 | 25 | 60 | <10 |
| 3 | 50:1 | 500 | 10 | 50 | 20 |
| 4 | 100:1 | 1000 | 10 | <10 | <10 |
| 5 | — | 250 | — | $2.4 \times 10^8$ | $4.3 \times 10^6$ |
| 6 | — | 500 | — | $1.4 \times 10^8$ | $2.6 \times 10^6$ |
| 7 | — | 1000 | — | $9.0 \times 10^7$ | $2.8 \times 10^5$ |
| 8 | — | 2000 | — | <10 | 40 |
| 9 | — | — | 10 | $10^8$ | $4 \times 10^5$ |
| 10 | — | — | 25 | $9.0 \times 10^7$ | $10^2$ |
| 11 | — | — | 50 | $2.5 \times 10^7$ | <10 |

As seen from the above examples, the antifungal and antibacterial combination described previously can have synergistic activity when employed at appropriate concentrations and may be used to inhibit the growth of fungi and bacteria in aqueous systems, such as metalworking fluids. It will be obvious to those skilled in the art that the required synergistically effective amount (concentration) will vary depending on the particular organisms and particular applications, and can readily be determined by routine experimentation. Use of a synergistically effective amount enables the use of a substantially smaller amount of each of components (a) and (b) to achieve a given effect than would be necessary for each component if used alone, or than would be necessary if a mere additive effect from combining (a) and (b) were obtained.

What is claimed is:

1. A composition comprising (a) hexahydro-1,3,5-tris(2-hydroxyethyl)-s-triazine and (b) an iodopropargyl compound selected from the group consisting of iodopropargyl carbamate and 3-iodopropargyl-N-butyl carbamate, said composition containing an amount of (a) and (b) synergistically effective to reduce the growth of bacteria, wherein the ratio of (a) to (b) is from about 1:1 to about 99:1.

2. A method of controlling the growth of bacteria in an aqueous fluid comprising the step of adding to said fluid a composition comprising (a) hexahydro-1,3,5-tris(2-hydroxyethyl)-s-triazine and (b) an iodopropargyl compound selected from the group consisting of iodopropargyl carbamate and 3-iodopropargyl-N-butyl carbamate in a synergistically effective amount to control said growth, wherein the ratio of (a) to (b) is from about 1:1 to about 99:1.

* * * * *